United States Patent
Hazin et al.

(10) Patent No.: US 8,193,387 B2
(45) Date of Patent: *Jun. 5, 2012

(54) PROCESS FOR PRODUCING AN UNSATURATED CARBOXYLIC ACID FROM AN ALKANE

(75) Inventors: Paulette N. Hazin, Sugar Land, TX (US); Frederick Merrill Galloway, Tomball, TX (US); John S. Ledford, Sugar Land, TX (US); Andy H. Nuyen, Houston, TX (US)

(73) Assignee: Saudi Basic Industries Corporation, Riyadh, (SA)

( * ) Notice: Subject to any disclaimer, the term of this patent is extended or adjusted under 35 U.S.C. 154(b) by 327 days.

This patent is subject to a terminal disclaimer.

(21) Appl. No.: 12/386,280

(22) Filed: Apr. 16, 2009

(65) Prior Publication Data

US 2009/0287019 A1    Nov. 19, 2009

Related U.S. Application Data

(63) Continuation-in-part of application No. 10/741,386, filed on Dec. 19, 2003, now abandoned.

(51) Int. Cl.
    *C07C 51/16* (2006.01)
(52) U.S. Cl. .......................................... 562/549
(58) Field of Classification Search .................. None
    See application file for complete search history.

(56) References Cited

U.S. PATENT DOCUMENTS

| | | | |
|---|---|---|---|
| 5,380,933 A * | 1/1995 | Ushikubo et al. | ............. 562/549 |
| 6,043,185 A | 3/2000 | Cirjak et al. | |
| 6,114,278 A | 9/2000 | Karim et al. | |
| 6,162,760 A | 12/2000 | Brazdil, Jr. | |
| 6,291,393 B1 | 9/2001 | Tu et al. | |
| 6,441,227 B1 | 8/2002 | Karim et al. | |
| 6,492,548 B1 | 12/2002 | Brockwell et al. | |
| 6,642,174 B2 | 11/2003 | Gaffney et al. | |
| 2002/0123647 A1 | 9/2002 | Bogan, Jr. et al. | |
| 2002/0188150 A1 | 12/2002 | Gaffney et al. | |

FOREIGN PATENT DOCUMENTS

EP    1193240    *    4/2002

* cited by examiner

*Primary Examiner* — Karl J Puttlitz
*(74) Attorney, Agent, or Firm* — Cantor Colburn LLP

(57) ABSTRACT

A one-step vapor phase oxidation process produces an unsaturated carboxylic acid, such as acrylic acid or methacrylic acid, from an alkane, such as propane or isobutane, with a mixed metal oxide catalyst and an excess of alkane relative to oxygen. The unreacted alkane and the byproduct alkene are recycled to the reaction zone without separation. Overall yield and productivity of the unsaturated carboxylic improves for such a process. An analogous method for the preparation of unsaturated nitrites is also disclosed.

26 Claims, 1 Drawing Sheet

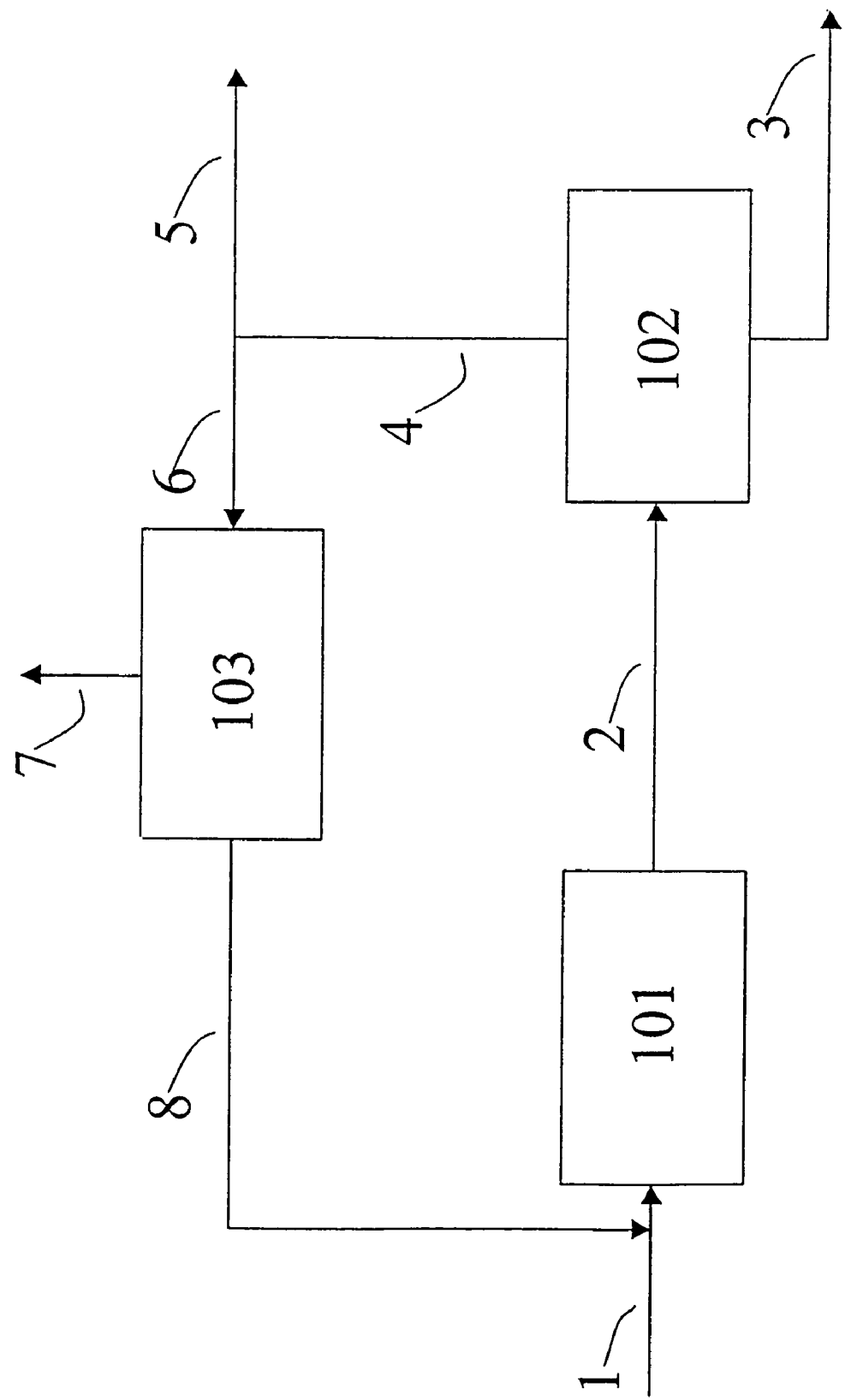

PROCESS FOR PRODUCING AN UNSATURATED CARBOXYLIC ACID FROM AN ALKANE

This is a continuation-in-part application of application Ser. No. 10/741,386 filed Dec. 19, 2003, now abandoned.

BACKGROUND OF THE INVENTION

1. Field of the Invention

This invention relates to a process for producing an unsaturated carboxylic acid from an alkane, in particular, a process for producing acrylic acid from propane by a single step vapor phase oxidation reaction with an excess of alkane relative to oxygen and with recycle of the unreacted alkane and the alkenes produced as byproducts of the reaction, particularly propylene.

2. Description of the Prior Art

The production of an unsaturated carboxylic acid, such as acrylic acid or methacrylic acid, is accomplished commercially by catalytically reacting an olefin, such as propylene or isobutylene, with oxygen to form an alkenylaldehyde, such as acrolein or methacrolein, which is subsequently catalytically reacted with oxygen. There are instances of producing acrylic acid and other unsaturated carboxylic acids from propane and other alkanes in a one step vapor phase catalytic oxidation reaction. Alkanes, such as propane, have advantages of cost and of availability over olefins.

Vapor phase catalytic oxidation of alkanes will, in addition to the unsaturated carboxylic acid, produce byproducts, including an alkene or olefin. For example, when the alkane is propane, byproducts of carbon monoxide, carbon dioxide, acetic acid and propylene will be formed. The olefin may be separated from the other byproducts and recycled into the reaction zone where the olefin can be converted into an unsaturated carboxylic acid, e.g., propylene into acrylic acid. In the alternative, the olefin may be separated from the other byproducts and converted to an unsaturated carboxylic acid in a separate process using known catalysts for converting an olefin into an unsaturated carboxylic acid or used in other processes to produce other products.

U.S. Pat. No. 6,642,174 discloses a mixed metal oxide catalyst for conversion by vapor phase oxidation of an alkane or a mixture of an alkane and an alkene to an unsaturated carboxylic acid or, in the presence of ammonia, to an unsaturated nitrile. The process for oxidation of propane or isobutane to acrylic acid or methacrylic acid may be practiced in a single pass mode or a recycle mode where at least a portion of the reactor effluent is returned to the reactor. The molar ratio of alkane or alkane/alkene mixture to oxygen in the starting material gas is disclosed as 1:0.1 to 10, more preferably 1:1 to 5.0.

U.S. Pat. No. 6,492,548 discloses processes for the oxidation of an alkane, such as propane, to form unsaturated carboxylic aldehydes and acids, such as acrolein and acrylic acid, in three steps, the first converting the alkane to the corresponding alkene and then converting the alkene to the corresponding unsaturated aldehyde and then converting the aldehyde to the corresponding unsaturated carboxylic acid. Unreacted propane, propylene, oxygen, carbon monoxide and carbon dioxide may be recycled to the propane-to-propylene reaction. Operating at low propane-to-propylene conversion makes the selectivity to propylene unexpectedly high and the presence of propane was found to enhance the efficiency of the propylene-to-acrolein reaction. The low-conversion, high-selectivity mode of operation is highly efficient provided that unreacted propane is recycled to the propane oxidation reactor. Propane and other noncondensed gases may be recycled without significant additional purification steps. The ratio of propane to oxygen is disclosed as being in the range from 5:1 to 40:1.

U.S. Pat. No. 6,441,227 discloses a two stage process for the production of alpha-beta carboxylic acids through catalytic vapor-phase oxidation of olefins with mixed metal oxide catalysts by oxidizing an olefin, such as propylene, to an aldehyde and then oxidizing the aldehyde to a carboxylic acid. Propane may be present as inert gas.

U.S. Pat. No. 6,114,278 discloses a mixed metal oxide catalyst containing Mo, V, Ga, Pd and Nb for a one-stage catalytic vapor phase partial oxidation of propane for production of acrylic acid. Non-reacted initial reactants may be recycled but less than 1% propylene is intended to be formed, more preferably, no detectable propylene is formed. The ratio of propane to oxygen is disclosed in the range of 1/5-5/1. Molar ratios for propane:oxygen:nitrogen were 20:10:70 in the working examples.

U.S. Pat. No. 5,380,933 discloses a method for producing an unsaturated carboxylic acid from an alkane by vapor phase catalytic oxidation with a mixed metal oxide catalyst. Recycle of propylene is not disclosed. The alkane:oxygen: diluting gas:$H_2O$ in the starting material gas is disclosed as preferably being 1:0.1 to 10.0:0 to 20:0.2 to 70, more preferably 1:1 to 5.0:0 to 10:5 to 40.

U.S. Pat. No. 6,291,393 discloses a metal oxide catalyst for producing acrylic acid by vapor phase catalytic oxidation of propane, propylene or acrolein. Unreacted propane and propylene as an intermediate may be recycled. The volumetric proportion of air to propane is disclosed as preferably 30 times or less, more preferably from 0.2 to 20 times.

U.S. Pat. No. 6,162,760 discloses a process for the ammoxidation of paraffins to unsaturated mononitriles in which unreacted propane and isobutane along with propylene and isobutene produced by the reaction are recycled for conversion to acrylonitrile and methacrylonitrile. The feed composition has a mole ratio of the paraffin to ammonia in the range of from about 2.5 to 16 and a mole ratio of paraffin to oxygen in the range of from about 1.0 to 10. The catalyst is a vanadium-antimony oxide catalyst containing at least one of titanium, tin, iron, chromium or gallium and at least one of molybdenum, tungsten, niobium, arsenic, tellurium or selenium.

U.S. Pat. No. 6,043,185 discloses a process for the ammoxidation of paraffins to unsaturated mononitriles in which unreacted propane and isobutane along with propylene and isobutene produced by the reaction are recycled for conversion to acrylonitrile and methacrylonitrile. The feed composition has a mole ratio of the paraffin to ammonia in the range of from about 1.0 to 10, preferably 2 to 4, and a mole ratio of paraffin to oxygen in the range of from about 1.0 to 10, preferably 1 to 3. The catalyst is a molybdenum-antimony-gallium mixed metal oxide catalyst.

U.S. Patent Application Publication no. 2002/0123647 discloses a method for producing an unsaturated carboxylic acid from an alkane with a mixed metal oxide catalyst. The unreacted alkane and the generated alkene are recycled to the reaction zone. An analogous method for the preparation of unsaturated nitriles is also disclosed. The molar ratio of alkane or mixture of alkane and alkene to oxygen to diluting gas to water is disclosed as (1):(0.1 to 10):(0 to 20):(0.1 to 70), preferably (1):(1 to 5.0):(0 to 10):(0.2 to 40).

SUMMARY OF THE INVENTION

The present invention is a one-step vapor phase oxidation process for producing an unsaturated carboxylic acid, such as acrylic acid or methacrylic acid, from an alkane, such as propane or isobutane, with a mixed metal oxide catalyst and an excess of alkane relative to oxygen. The alkane:oxygen molar ratio is greater than the stoichiometric molar ratio. The present invention is for a method for producing an unsaturated carboxylic acid comprising: (a) contacting an alkane and an oxygen-containing gas with a catalyst containing a mixed metal oxide in a reaction zone under conditions which produce a product gas comprising said unsaturated carboxylic acid, unreacted alkane and a byproduct alkene; (b) recovering unreacted alkane and byproduct alkene from said product gas; and (c) recycling said recovered unreacted alkane and byproduct alkene to said reaction zone;
wherein said mixed metal oxide has the formula:

$$MoV_vA_aB_bC_cO_x$$

Mo is molybdenum, V is vanadium, A, B and C are each niobium, antimony, tellurium, silver, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, selenium, palladium, gallium, zinc, praseodymium, rhenium, iridium, neodymium, yttrium, samarium and terbium, v is 0.1 to 0.5, a is 0.01 to 0.2, b is 0.0 to 0.5, c is 0.0 to 0.5, x is determined by the valence requirements of the other components and wherein the alkane:oxygen molar ratio is from about 3:1 to about 1:1.

The essential elements of the present invention are that it is a one-step alkane-to-unsaturated carboxylic acid process in which there is an excess of alkane relative to oxygen and in which unreacted alkane and byproduct alkene are recycled to the reaction zone without separation of the alkene and the alkane.

BRIEF DESCRIPTION OF THE DRAWINGS

A more complete appreciation of the invention and many of the attendant advantages thereof will be readily understood by reference to the following detailed description when considered in connection with the accompanying drawing:

The FIGURE is a flowsheet illustrating an embodiment of the invention.

DETAILED DESCRIPTION OF THE INVENTION

Much research has been performed for the catalytic oxidation of propane to produce acrylic acid; however, no industrial process has yet been practiced commercially. Most of the research has focused on high conversion of propane per pass in order to reduce or eliminate the need for recycle of unreacted propane. The concentration of propane in the feed is kept low because of the need for more oxygen to achieve high conversion, and water and inert diluent are added to increase selectivity. At high conversion, the selectivity to acrylic acid has not been sufficient for satisfactory industrial performance. Higher selectivity is achieved by reducing the conversion of propane per pass, but then the catalyst productivity (Kgproduct/m³cat-hr) is too low for satisfactory industrial performance.

A solution to these problems is presented by the claimed invention. A catalyst and reaction conditions for the single step oxidation of propane have been found in which the combined selectivity to acrylic acid and propylene are high at low propane conversion per pass. At the same time, the concentration of propane in the feed is such that the catalyst productivity is high enough for satisfactory industrial performance. It has also been discovered under these conditions a co-feed of propane plus propylene can be converted to acrylic acid with higher total selectivity than the selectivity to acrylic acid for propane alone. Thus, by recycling unreacted propane and the byproduct propylene to the reactor, essentially without separation from each other, the over-all yield of acrylic acid from fresh propane feed is also satisfactory for industrial performance.

It has been determined that a one-step vapor phase catalytic oxidation using a mixed metal oxide catalyst in which a feed having an excess of alkane relative to oxygen in combination with recycle to the reaction zone of the unreacted alkane and the alkene produced as a byproduct of the reaction achieves increased productivity of unsaturated carboxylic acid. The one-step vapor phase catalytic oxidation includes conversion of an alkane feed to an unsaturated carboxylic acid but with an excess of alkane relative to oxygen which in the first instance decreases the conversion of propane and the yield of the unsaturated carboxylic acid and increases selectivity to and yield of alkene byproduct. While the excess of alkane relative to oxygen would appear to produce the opposite of the desired result, i.e., increased acrylic acid conversion and yield, recycle of the unreacted alkane and the byproduct alkene, both of which are also converted to an unsaturated carboxylic acid, improves the overall productivity, i.e., kilograms of product per cubic meter of catalyst per hour (Kg/m³cat-hr). Since most or all of the recycled alkene byproduct is converted to unsaturated carboxylic acid, the overall selectivity of the process to unsaturated carboxylic acid is increased.

The alkane is preferably one having three to eight carbon atoms and is most preferably propane or isobutane. The process is preferably a vapor phase reaction in which a catalyst is brought into contact with an alkane and oxygen. The molar ratio of alkane:oxygen is preferably in the range of from 3:1 to 1:1. In one embodiment of the present invention the molar ratio of alkane:oxygen is about 2:1.

Other feed components, such as inert gases, carbon dioxide, methane and water may be added to the reaction gases. If water is present, it may be as steam and the molar ratio of alkane:steam is in the range from 0.05:1 to 10:1. An inert gas such as carbon dioxide, methane, nitrogen, argon or helium may be used as a carrier medium. If a carrier medium is used, the molar ratio of alkane:carrier preferably is in the range from 0.1:1 to 10:1.

The oxidative reaction of propane to acrylic acid is as follows:

$$C_2H_3CH_2CH_3 + 2O_2 \rightarrow CH_2CHCOOH + 2H_2O$$

The stoichiometric molar ratio for propane:oxygen is 1:2 (0.5:1). An excess of propane relative to oxygen would be a molar ratio of propane:oxygen of more than 0.5:1. In one embodiment of the present invention the molar ratio of propane:oxygen is in the range of from 3:1 to 0.625:1. In another embodiment of the present invention the molar ratio of propane:oxygen is in the range of from 3:1 to 1:1. In another embodiment of the present invention the molar ratio of propane:oxygen is in the range of from 2:1 to 1:0.625:1. In another embodiment of the present invention the molar ratio of propane:oxygen is in the range of from 2:1 to 1:1. In another embodiment of the present invention the molar ratio of propane:oxygen is about 2:1.

The reaction temperature for the method of using the present invention is 320-450° C., preferably 350-410° C. The reaction pressure is 0 to 75 psig, preferably 5 to 50 psig.

The method of the present invention will produce byproducts, including an alkene or olefin, in addition to the unsaturated carboxylic acid product. For example, when the alkane is propane, byproducts of carbon monoxide, carbon dioxide, acetic acid and propylene will be formed. It is not necessary to separate the alkene, such as propylene, from the other byproducts, but separation of carbon oxides and other diluent or inert gases may be advantageous to prevent buildup of these gases in the process. Separation of the alkene from the alkane is neither necessary nor desirable for the process of this invention. It is preferable that the alkene be recycled into the feed stream. A typical but nonlimiting amount of alkene which is recycled to the reactor feed is within an alkane:alkene molar ratio of 1:0.02 to 1:0.2, preferably 1:0.03 to 1:0.1, more preferably 1:0.04 to 1:0.1. The catalyst and process of the present invention can convert an alkene into an unsaturated carboxylic acid, e.g., propylene into acrylic acid. Without being limited by theory, it is believed that a process which produces an unsaturated carboxylic acid as the desired product from an alkane will not generate more than 25% of an alkene as a percent of total hydrocarbon for recycle.

The gas space velocity of the claimed vapor phase process depends on reactor size and design. In one embodiment of the present invention the gas space velocity in the vapor phase reaction is greater than 2000 hr$^{-1}$. A laboratory embodiment may have gas space velocity in the range from about 10,000 to about 15,000 hr$^{-1}$. An industrial scale embodiment may have gas space velocity in the range from about 2000 to about 5000 hr$^{-1}$. The contact time for the reactants preferably is in the range of from 0.1 to 2.0 seconds, preferably 0.2 to 1.0 seconds.

The present invention provides a method for producing an unsaturated carboxylic acid comprising: (a) contacting an alkane and oxygen in a molar ratio from about 3:1 to about 1:1 in the presence of a mixed metal oxide catalyst under conditions which produce a product gas comprising an unsaturated carboxylic acid, unreacted alkane and a byproduct alkene; (b) recovering unreacted alkane and byproduct alkene from the product gas; and (c) recycling the recovered unreacted alkane and byproduct alkene to the reaction zone.

The mixed metal oxide catalyst for the oxidation process described above has the general formula:

$$MoV_vA_aB_bC_cO_x$$

Mo is molybdenum, V is vanadium, A, B and C are each niobium, antimony, tellurium, silver, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, selenium, palladium, gallium, zinc, praseodymium, rhenium, iridium, neodymium, yttrium, samarium and terbium, v is 0.1 to 0.5, a is 0.01 to 0.2, b is 0.0 to 0.5, c is 0.0 to 0.5, x is determined by the valence requirements of the other components.

One embodiment of the catalyst of the present invention has the composition described in the following formula:

$$MoV_aNb_bTe_cSb_dM_eO_x$$

wherein optional element M may be one or more selected from silver, silicon, sulfur, zirconium, titanium, aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum; a is 0.05 to 0.99 or 0.1 to 0.5 or 0.3; b is 0.01 to 0.99 or 0.05 to 0.2 or 0.05 to 0.12; c is 0.01 to 0.5 or 0.01 to 0.12 or 0.01 to 0.10; d is 0 to 0.2 or 0.01 to 0.15 or 0.03 to 0.1; e is 0 to 0.5 or 0.01 to 0.25 or 0.02 to 0.1; and x is determined by the valence requirements of the other components of the catalyst composition.

Another embodiment of the catalyst of the present invention has the composition described in the following formula:

$$MoV_aNb_bM_cO_x$$

wherein Mo is molybdenum, V is vanadium, Nb is niobium and M is one or more elements selected from the group consisting of antimony, tellurium, silver, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, selenium, palladium, gallium, zinc, praseodymium, rhenium, iridium, neodymium, yttrium, samarium and terbium; a is 0.05 to 0.99; b is 0.01 to 0.99; c is 0.0 to 0.5; and x is determined by the valence requirements of the other components of the catalyst composition. Specific examples of M are tellurium, antimony, silver, bismuth, gallium and potassium. Other specific examples of M are tellurium alone or in combination with antimony, silver alone or in combination with antimony, bismuth in combination with antimony, gallium in combination with antimony and potassium in combination with antimony. M may be present in the range from about 0.01 to about 0.25.

The present invention also provides a method for producing an unsaturated nitrile comprising: (a) contacting an alkane, ammonia and oxygen in a molar ratio from about 3:1 to about 1:1 in the presence of a mixed metal oxide catalyst under conditions which produce a product gas comprising the product unsaturated nitrile, unreacted alkane and a product alkene; (b) recovering unreacted alkane and product alkene from the product gas; and (c) recycling the recovered unreacted alkane and product alkene to the reaction zone.

The mixed metal oxide for the ammoxidation process is a catalyst known in the art for converting an alkane in the presence of ammonia and water to an unsaturated nitrile. One embodiment of the catalyst may have the general formula:

$$V_aM_bM'_cO_x$$

wherein V is vanadium, M is at least one element selected from molybdenum, antimony, magnesium, aluminum, zirconium, silicon, hafnium, titanium and niobium, M' is at least one element selected from tellurium, rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium, a is 0 to 4, b is 0 to 15, c is 0 to 15, and x is determined by the valence requirements of the elements present.

The invention having been generally described, the following examples are given as particular embodiments of the invention and to demonstrate the practice and advantages thereof. It is understood that the examples are given by way of illustration and are not intended to limit the specification or the claims to follow in any manner.

Catalyst Preparation

Catalyst 1

A mixed metal oxide with a nominal composition of $Mo_{1.0}V_{0.3}Nb_{0.12}Te_{0.23}O_x$ was prepared as follows:

Solution A: In 400 mL of warm water 40.11 g ammonium paramolybdate were dissolved, followed by 7.97 g of ammonium vanadate. Telluric acid dihydrate (12.0 g) were dissolved next. The solution was allowed to cool to ambient temperature.

Solution B: In 110 mL of water 20.62 g of oxalic acid dihydrate and 4.65 g of niobic acid were heated for one hr to form a uniform solution. The solution was allowed to cool to ambient temperature.

Solution B was added to solution A. The slurry was spray dried using an inlet temperature of 200° C. and an outlet temperature of 110° C. to obtain a solid product.

The solid product was calcined in air for 5 hours at 300° C. then in a stream of argon at 600° C. for 2 hrs. The solid was then crushed, pressed and sieved. The fraction of 18 to 35 mesh was tested.

Catalyst 2

A mixed metal oxide with a nominal composition of $Mo_1V_{0.3}Nb_{0.05}Sb_{0.15}Te_{0.06}O_x$ was prepared as follows:

Solution A: Ammonium vanadate (7.95 g) was dissolved in 165 mL water at 91° C. The solution was purged with nitrogen. Antimony (III) oxide (4.92 g) was added and the mixture was purged with nitrogen and heated at 91° C. for 4 hrs. The mixture was cooled in ice to 19° C. Ammonium paramolybdate (40.0 g) was added and the mixture was stirred under nitrogen overnight.

Solution B: Niobium oxalate mono oxalate (7.12 g) was stirred in 40 mL water overnight.

Solution C: Telluric acid dihydrate (3.12 g) was dissolved in 40 ml of water with heating. Solution C was cooled to room temperature.

Solution B was added to solution A followed by solution C. The resulting mixture was spray dried at an outlet temperature of 99° C. to give a solid catalyst precursor. The catalyst precursor was heated in air at 120° C. for 1 hr, then heated at 300° C. for 5 hrs, then calcined in argon at 600° C. for 2 hrs. The resulting powder was ground pressed and sieved. The 18/35 mesh fraction was tested.

Catalyst 3

A mixed metal oxide with a nominal composition of $Mo_1V_{0.3}Nb_{0.05}Sb_{0.15}Te_{0.06}O_x$ was prepared as follows:

Solution A: Ammonium vanadate (7.95 g) was dissolved in 165 mL water at 92° C. Antimony (III) oxide (4.92 g) was added and the mixture was purged with nitrogen and heated at 92° C. for 4 hrs. The mixture was cooled to room temperature overnight.

Solution B: Ammonium paramolybdate (40.0 g) was dissolved in 100 ml water with heating. Telluric acid dihydrate (3.12 g) was added next and was dissolved. Solution B was cooled to room temperature.

Solution C: In 165 mL of water 20.62 g of oxalic acid dihydrate and 4.65 g of niobic acid were heated for forty five minutes to form a uniform solution. The solution was allowed to cool to ambient temperature.

Solution B was added to solution A followed by solution C. The resulting mixture was spray dried at an outlet temperature of 100° C. to give a solid catalyst precursor. The catalyst precursor was heated in air at 120° C. for 1 hr, then heated at 300° C. for 5 hrs, then calcined in argon at 600° C. for 2 hrs. The resulting powder was ground pressed and sieved. The 18/35 mesh fraction was tested.

Catalyst Testing

In the following examples the specified catalyst in the specified amount was mixed with enough quartz chips to make a 5 cc catalyst bed. The resulting mixture was placed into a down-flow packed bed reactor. All the catalyst were tested using propane unless otherwise noted, 10% by volume oxygen in nitrogen, and steam in the by volume ratio specified in table 1 for each example. The reaction continued at the specified conditions for at least 3 hours. The % conversion and % selectivity results are reported in Table 1. Also reported in Table 1 is the productivity of acrylic acid for each example as measured by the kilograms of acrylic acid produced per cubic meter of catalyst in one hour ($KgAA/m^3cat-hr$).

Example 1

1 g of the mixed metal oxide prepared in as Catalyst 1 above was tested for propane oxidation as illustrated in Table 1.

Example 2

1 g of the mixed metal oxide prepared in Catalyst 1 above was tested for propane oxidation as illustrated in Table 1.

Example 3

1 g of the mixed metal oxide prepared in Catalyst 1 above was tested for propane oxidation as illustrated in Table 1.

Example 4

2.7 g of the mixed metal oxide prepared in Catalyst 2 above was tested for propane oxidation as illustrated in Table 1.

Example 5

2.7 g of the mixed metal oxide prepared in Catalyst 2 above was tested for propane oxidation as illustrated in Table 1.

Example 6

1 g of the mixed metal oxide prepared in Catalyst 3 above was tested for propane oxidation as illustrated in Table 1.

Example 7

1 g of the mixed metal oxide prepared in Catalyst 3 above was tested for propane oxidation as illustrated in Table 1.

Comparative Example 1

3.4 g of the mixed metal oxide prepared in Catalyst 1 above was tested for propane oxidation as illustrated in Table 1.

Comparative Example 2

2.7 g of the mixed metal oxide prepared in Catalyst 3 above was tested for propane oxidation as illustrated in Table 1.

TABLE 1

| Example | Catalyst Amount (g) | T (° C.) | P-PSIG | SV-g propane/g cat-hr | Reaction Time (sec) | % Con | % $Co_x$ | % Sel $C_{3=}$ | % Sel AA | % AA Yield | $KgAA/m^3$ cat-hr | $P:O_2$ | $H_2O/P$ | Sel. to $C_{3=}$ + AA |
|---|---|---|---|---|---|---|---|---|---|---|---|---|---|---|
| | | | | | $MoV_{0.3}Nb_{0.12}Te_{0.23}$ | | | | | | | | | |
| 1 | 1 | 400 | 32 | 2.31 | 0.31 | 23 | 13.1 | 13.5 | 60.5 | 14.0 | 731 | 1:0.5 | 3.4 | 74.0 |
| 2 | 1 | 400 | 20 | 2.31 | 0.23 | 19 | 8.6 | 18.1 | 65.2 | 12.7 | 623 | 1:0.5 | 3.4 | 83.3 |
| 3 | 1 | 400 | 32 | 0.52 | 0.41 | 38 | 11.1 | 7.4 | 72.3 | 27.3 | 315 | 1:1.6 | 14.9 | 79.6 |
| Comp. 1 | 3.4 | 400 | 20 | 0.11 | 1.07 | 72 | 25.8 | 1.6 | 65.5 | 47.1 | 121 | 1:3.0 | 14.0 | 67.1 |

TABLE 1-continued

| Example | Catalyst Amount (g) | T (° C.) | P-PSIG | SV-g propane/ g cat-hr | Reaction Time (sec) | % Con | % $CO_x$ | % Sel $C_{3=}$ | % Sel AA | % AA Yield | KgAA/$m^3$ cat-hr | P:$O_2$ | $H_2O$/P | Sel. to $C_{3=}$ + AA |
|---|---|---|---|---|---|---|---|---|---|---|---|---|---|---|
| $MoV_{0.3}Nb_{0.05}Sb_{0.15}Te_{0.06}$ | | | | | | | | | | | | | | |
| 4 | 2.7 | 400 | 20 | 0.82 | 0.59 | 21 | 14.5 | 15.2 | 54.1 | 11.6 | 228 | 1:0.5 | 3.4 | 69.3 |
| 5 | 2.7 | 400 | 20 | 0.15 | 1.00 | 52 | 23.6 | 3.6 | 56.3 | 29.2 | 105 | 1:1.6 | 14.9 | 59.9 |
| $MoV_{0.3}Nb_{0.05}Sb_{0.09}Te_{0.09}$ | | | | | | | | | | | | | | |
| 6 | 1 | 420 | 32 | 2.29 | 0.27 | 19 | 11.2 | 20.6 | 60.0 | 11.6 | 659.3 | 1:0.5 | 3.4 | 80.6 |
| 7 | 1 | 420 | 32 | 0.26 | 0.70 | 52 | 23.3 | 4.8 | 62.6 | 32.4 | 216 | 1:1.6 | 14.9 | 67.4 |
| Comp. 2 | 2.7 | 410 | 32 | 0.1 | 1.28 | 80 | 34.1 | 1.3 | 52.1 | 41.5 | 107 | 1:3.0 | 14 | 53.4 |

P = Propane SV = Space Velocity $C_{3=}$ = Propylene AA = Acrylic Acid % Con = per cent conversion Sel = selectivity % $CO_x$ = per cent carbon monoxide + carbon dioxide The relevant portions of Table 1 are extracted below:

| Catalyst | Example | Propane/Oxygen mole ratio | Productivity (KgAA/$m^3$cat · hr) |
|---|---|---|---|
| $MoV_{0.3}Nb_{0.12}Te_{0.23}$ | 1 | 2:1(1:0.5) | 731 |
| | 2 | 2:1(1:0.5) | 623 |
| | 3 | 0.625:1(1:1.6) | 315 (propane-rich) |
| | Comp. 1 | 0.33:1(1:3) | 121 (oxygen-rich) |
| $MoV_{0.3}Nb_{0.05}Sb_{0.15}Te_{0.06}$ | 4 | 2:1(1:0.5) | 228 |
| | 5 | 0.625:1(1:1.6) | 105 |
| $MoV_{0.3}Nb_{0.05}Sb_{0.09}Te_{0.09}$ | 6 | 2:1(1:0.5) | 659.3 |
| | 7 | 0.625:1(1:1.6) | 216 (propane-rich) |
| | Comp. 2 | 0.33:1(1:3) | 107 (oxygen-rich) |

As can be seen from the data above, a feed with a more propane than the stoichiometric molar ratio, e.g., a propane:oxygen mole ratio in the range of from 2:1 to 0.625:1 (propane-rich) as in Examples 1-7 results in better productivity for acrylic acid than a feed with a more oxygen than the stoichiometric molar ratio, e.g., a propane:oxygen mole ratio of 0.33:1 (oxygen-rich) as in Comparative Examples 1 and 2, for different catalysts within the claimed invention. The propane:oxygen mole ratio of the feed of the Examples, demonstrate a productivity of at least twice that of the Comparative Examples.

While the one-pass acrylic acid yield for an excess of propane to oxygen is not as high as that for an excess of oxygen to propane, the productivity of acrylic acid (KgAA/$m^3$cat-hr) increases and propylene which can be converted to acrylic acid, as the following examples show, is also generated.

Experiments Using Mixed Propane/Propylene Feed:

Examples 8-12

A mixed metal oxide with a nominal composition of $Mo_1V_{0.3}Nb_{0.05}Sb_{0.15}Ag_{0.06}O_x$ was prepared as follows:

Solution A: Ammonium vanadate (15.9 g) was dissolved in 320 mL water with heating. Antimony (III) oxide (9.91 g) was added and the mixture was purged with nitrogen and heated at 97° C. for about 5 hrs. Heating was discontinued and the mixture was cooled overnight under nitrogen. Some of the water (272 mL) was removed by rotary evaporation. Ammonium paramolybdate (80.2 g) was added and the mixture was stirred for 4.5 hrs under nitrogen.

Solution B: Niobium oxalate mono oxalate (14.23 g) was stirred in 80 mL water for 3 hrs.

Solution C: silver nitrate (4.62 g) was dissolved in 40 mL water. Solution B was added to solution A followed by solution C, and the resulting mixture kept under nitrogen for 7 minutes until it was spray dried to give a solid catalyst precursor.

The catalyst precursor was heated in air at 120° C. for 1 hr, then heated at 300° C. for 5 hrs, then calcined in argon at 600° C. for 2 hrs. The resulting powder was ground pressed and sieved to 18/35 mesh. 1.8 g of this catalyst was tested for propane/propylene oxidation using 10% by volume oxygen nitrogen mixture as described in examples 8-12 in Table 2. The same amount of propane feed (20 cc/min) was used in each example and propylene was added as indicated.

TABLE 2

| | | | | | % Selectivity | | | | |
|---|---|---|---|---|---|---|---|---|---|
| Example | % $C_3H_8$ in $C_3$ feed | % $C_3H_6$ in $C_3$ feed | Conversion of $C_3$ Feed | % $CO_x$ | Propylene Produced in effluent | Acetic Acid | Acrylic Acid | Acrylic Acid Yield | Acrylic Acid Productivity* (KgAA/$m_3$-hr) |
| 8 | 100.0 | 0.0 | 13.2 | 11.9 | 19.7 | 10.2 | 54.4 | 7.2 | 241.5 |
| 9 | 97.1 | 2.9 | 15.0 | 12.2 | 18.1 | 10.2 | 55.2 | 8.3 | 282.9 |
| 10 | 95.2 | 4.8 | 15.8 | 12.5 | 17.3 | 10.5 | 55.3 | 8.7 | 307.5 |
| 11 | 90.9 | 9.1 | 19.4 | 13.3 | 14.6 | 12.6 | 56.5 | 11.0 | 400.9 |
| 12 | 87.0 | 13.0 | 20.4 | 12.4 | 16.4 | 11.8 | 55.8 | 11.4 | 436.5 |

Temperature = 380° C., pressure = 32 Psig, feed composition propane/$O_2$/$H_2O$/$N_2$ = 1/0.5/3.5/4.5, propylene in $C_3$ variable as indicated in the table, contact time 0.4, The data in Table 2 above for a high propane:oxygen ratio (1:0.5) feed demonstrates that the introduction of propylene into a propane-to-acrylic acid conversion process improves the yield and productivity of acrylic acid. As the amount of propylene increases in the reactor feed, the conversion of total $C_3$ components (propane+propylene) increases. The data in Table 2 above shows that the alkene is very reactive. Despite the increase in alkene concentration in the feed, there was no increase in propylene concentration in the effluent stream.

Catalyst Preparation

Catalyst 4

A mixed metal oxide with a nominal composition of $Mo_{1.0}V_{0.2}Nb_{0.12}Ag_{0.25}O_x$ was prepared as follows:

Solution A: In 600 mL of warm water 60.03 g ammonium paramolybdate were dissolved, followed by 7.95 g of ammonium vanadate. The solution was allowed to cool to ambient temperature.

Solution B: In 200 mL of water 30.86 g of oxalic acid dihydrate and 6.96 g of niobic acid were heated for 45 minutes to form a uniform solution. The solution was allowed to cool to ambient temperature.

Solution C: Silver nitrate (13.38 g) was dissolved in 60 mL of water at ambient temperature.

Solution B was added to solution A with stirring followed by solution C to obtain a slurry. The slurry was stirred overnight. Water was evaporated from the slurry at 50° C. to form a paste. The paste was dried in the oven for several days to from a solid product.

The solid product was calcined in air for 5 hours at 300° C. then in a stream of argon at 600° C. for 2 hrs. The solid was then crushed, pressed and sieved. The fraction of 18 to 35 mesh was tested.

Catalyst 5

A mixed metal oxide with a nominal composition of $Mo_1V_{0.3}Nb_{0.05}Sb_{0.15}Bi_{0.03}Ox$ was prepared as follows Solution A: Ammonium vanadate (7.95 g) was dissolved in 165 mL water with heating. Antimony (III) oxide (4.92 g) was added and the mixture was heated at 95° C. for 4 hrs. Heating was discontinued and the mixture was cooled under nitrogen atmosphere overnight. Water (109 g) was removed by rotary evaporation. Ammonium paramolybdate solid (40.0 g) was added and the mixture was stirred for 4 hrs. Solution B: Niobium oxalate mono oxalate (7.12 g) was stirred in 40 mL water for 4 hrs. Solution C: Bismuth nitrate pentahydrate (3.298 g) was suspended in 60 mL water for 4 hrs. Solution B was added to solution A followed by solution C, and the resulting mixture was spray dried after 5 minutes to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh.

Catalyst 6

A mixed metal oxide with a nominal composition of $Mo_1V_{0.3}Nb_{0.05}Sb_{0.15}Ga_{0.03}Ox$ was prepared as follows:

Solution A: Ammonium vanadate (7.95 g) was dissolved in 165 mL water at 90° C. Antimony (III) oxide (4.91 g) was added and the mixture was heated at 98° C. for about 5 hrs. Heating was discontinued and the mixture was cooled. Some of the water was removed by rotary evaporation. Ammonium paramolybdate (40.0 g) was added and the mixture was stirred overnight.

Solution B: Niobium oxalate mono oxalate (7.12 g) was stirred in 40 mL water overnight.

Solution C: Gallium oxide (0.645 g) was stirred in 20 mL water overnight. Solution B was added to solution A followed by solution C, and the resulting mixture was spray dried after 20 minutes to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh.

Catalyst 7

A mixed metal oxide with a nominal composition of $Mo_1V_{0.3}Nb_{0.05}Sb_{0.15}Ag_{0.06}Ox$ was prepared as follows:

Solution A: Ammonium vanadate (7.95 g) was dissolved in 165 mL water with heating. Antimony (III) oxide (4.92 g) was added and the mixture was purged with nitrogen and heated at 95° C. for about 5 hrs. Heating was discontinued and the mixture was cooled overnight under nitrogen. Some of the water (130 mL) was removed by rotary evaporation. Ammonium paramolybdate (40.0 g) was added and the mixture was stirred for 4 hrs under nitrogen. Solution B: Niobium oxalate mono oxalate (7.12 g) was stirred in 40 mL water overnight. Solution C: silver nitrate (2.31 g) was dissolved in 20 mL water. Solution B was added to solution A followed by solution C, and the resulting mixture kept under nitrogen for 20 minutes until it was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh.

Catalyst 8

A mixed metal oxide with a nominal composition of $Mo_1V_{0.3}Nb_{0.05}Sb_{0.15}K_{0.015}Ox$ was prepared as follows:

Solution A: Ammonium vanadate (7.95 g) was dissolved in 165 mL water with heating. Antimony (III) oxide (4.95 g) was added and the mixture was heated at 92° C. for about 5 hrs. Heating was discontinued and the mixture was cooled overnight under nitrogen. Some of the water (150 mL) was removed by rotary evaporation at 50° C. Ammonium paramolybdate (40.0 g) was added and the mixture was stirred for 4.5 hrs under nitrogen. Solution B: Niobium oxalate mono oxalate (7.12 g) was stirred in 40 mL water overnight. Solution C: Potassium hydrogen carbonate (0.34 g) was dissolved in 20 mL water. Solution B was added to solution A followed by solution C, and the resulting mixture stirred for 5 minutes until it was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh.

Catalyst Testing

In the following examples the specified catalyst in the specified amount was mixed with enough quartz chips to make a 5 cc catalyst bed. The resulting mixture was placed into a down-flow packed bed reactor. All the catalyst were tested using propane unless otherwise noted, 10% by volume oxygen in nitrogen, and steam in the by volume ratio specified in table 1 for each example. The reaction continued at the specified conditions for at least 3 hours. The % conversion and % selectivity results are reported in Table 1. Also reported in Table 1 is the productivity of acrylic acid for each example as measured by the kilograms of acrylic acid produced per cubic meter of catalyst in one hour ($KgAA/m^3cat$-hr).

Example 13

2.2 g of the mixed metal oxide prepared in as Catalyst 4 above was tested for propane oxidation as illustrated in Table 3.

Example 14

2.2 g of the mixed metal oxide prepared in Catalyst 4 above was tested for propane oxidation as illustrated in Table 3.

Comparative Example 3

2.2 g of the mixed metal oxide prepared in Catalyst 4 above was tested for propane oxidation as illustrated in Table 1.

Comparative Example 4

2.2 g of the mixed metal oxide prepared in Catalyst 4 above was tested for propane oxidation as illustrated in Table 3.

Example 15

1 g of the mixed metal oxide prepared in Catalyst 5 above was tested for propane oxidation as illustrated in Table 3.

Comparative Example 5

1 g of the mixed metal oxide prepared in Catalyst 5 above was tested for propane oxidation as illustrated in Table 3.

Example 16

1 g of the mixed metal oxide prepared in Catalyst 5 above was tested for propane oxidation as illustrated in Table 3.

Comparative Example 6

1 g of the mixed metal oxide prepared in Catalyst 5 above was tested for propane oxidation as illustrated in Table 3.

Example 17

1 g of the mixed metal oxide prepared in Catalyst 6 above was tested for propane oxidation as illustrated in Table 3.

Comparative Example 7

1 g of the mixed metal oxide prepared in Catalyst 6 above was tested for propane oxidation as illustrated in Table 3.

Example 18

1.8 g of the mixed metal oxide prepared in as Catalyst 7 above was tested for propane oxidation as illustrated in Table 3.

Example 19

1.8 g of the mixed metal oxide prepared in Catalyst 7 above was tested for propane oxidation as illustrated in Table 3.

Example 20

1.8 g of the mixed metal oxide prepared in as Catalyst 7 above was tested for propane oxidation as illustrated in Table 3.

Example 21

1.8 g of the mixed metal oxide prepared in Catalyst 7 above was tested for propane oxidation as illustrated in Table 3.

Comparative Example 8

1.8 g of the mixed metal oxide prepared in Catalyst 7 above was tested for propane oxidation as illustrated in Table 3.

Example 22

2.7 g of the mixed metal oxide prepared in Catalyst 8 above was tested for propane oxidation as illustrated in Table 3.

Comparative Example 9

2.7 g of the mixed metal oxide prepared in Catalyst 8 above was tested for propane oxidation as illustrated in Table 3.

TABLE 3

| Example | Catalyst Amount (g) | T (° C.) | P - PSIG | SV-g propane/ g cat-hr | Reaction Time (sec) | % Con | % $CO_x$ | % Sel $C_{3=}$ | % Sel AA | % AA Yield | KgAA/ $m^3$cat-hr | $P:O_2$ | $H_2O/P$ | Sel. to $C_{3=}$ + AA |
|---|---|---|---|---|---|---|---|---|---|---|---|---|---|---|
| $MoV_{0.2}Nb_{0.12}Ag_{0.23}$ | | | | | | | | | | | | | | |
| 13 | 2.2 | 400 | 32 | 0.99 | 0.55 | 17 | 13.6 | 17.2 | 57.9 | 9.8 | 292 | 1:0.5 | 3.4 | 75.2 |
| 14 | 2.2 | 400 | 32 | 0.50 | 0.58 | 20 | 16.1 | 13.7 | 60.5 | 12.4 | 183 | 1:1.0 | 6.9 | 74.2 |
| Comp. 3 | 2.2 | 400 | 32 | 0.26 | 0.59 | 22 | 20.6 | 12.7 | 57.8 | 12.8 | 97 | 1:2.0 | 13.7 | 70.5 |
| Comp. 4 | 2.2 | 400 | 32 | 0.17 | 0.72 | 28 | 24.0 | 9.6 | 57.2 | 15.9 | 76 | 1:3.0 | 14.0 | 66.8 |
| $MoV_{0.3}Nb_{0.05}Sb_{0.15}Bi_{0.03}$ | | | | | | | | | | | | | | |
| 15 | 1.0 | 410 | 20 | 2.16 | 0.23 | 20 | 12.2 | 18.6 | 54.6 | 10.8 | 562.9 | 1:0.5 | 3.4 | 73.2 |
| Comp. 5 | 1.0 | 410 | 20 | 0.35 | 0.30 | 40 | 19.1 | 7.3 | 55.5 | 22.4 | 195.0 | 1:3.0 | 14.0 | 62.8 |
| 16 | 1.0 | 400 | 32 | 0.50 | 0.40 | 34 | 21.3 | 9.0 | 53.5 | 18.1 | 209.2 | 1:1.6 | 14.9 | 62.5 |
| Comp. 6 | 1.0 | 400 | 32 | 0.18 | 0.80 | 64 | 33.6 | 2.6 | 48.1 | 30.8 | 130.7 | 1:3.0 | 14.0 | 50.7 |
| $MoV_{0.3}Nb_{0.05}Sb_{0.15}Ga_{0.03}$ | | | | | | | | | | | | | | |
| 17 | 1.0 | 380 | 20 | 0.62 | 0.21 | 30 | 16.1 | 9.2 | 57.7 | 17.2 | 313 | 1:1.6 | 14.8 | 66.9 |
| Comp. 7 | 1.0 | 380 | 20 | 0.36 | 0.26 | 40 | 20.3 | 6.6 | 57.8 | 22.9 | 229 | 1:3.0 | 14.0 | 64.4 |
| $MoV_{0.3}Nb_{0.05}Sb_{0.15}Ag_{0.06}$ | | | | | | | | | | | | | | |
| 18 | 1.8 | 360 | 20 | 1.23 | 0.44 | 13 | 11.6 | 18.7 | 57.1 | 7.6 | 280 | 1:0.5 | 1.3 | 75.7 |
| 19 | 1.8 | 360 | 20 | 1.23 | 0.38 | 13 | 10.7 | 18.9 | 57.6 | 7.2 | 268 | 1:0.5 | 2.5 | 76.6 |
| 20 | 1.8 | 360 | 20 | 1.23 | 0.34 | 14 | 10.1 | 19.1 | 56.5 | 8.0 | 247 | 1:0.5 | 3.4 | 75.6 |
| 21 | 1.8 | 400 | 20 | 0.36 | 0.33 | 35 | 21.7 | 7.3 | 57.9 | 20.4 | 213 | 1:1.6 | 14.9 | 65.2 |
| Comp. 8 | 1.8 | 380 | 20 | 0.19 | 0.44 | 39 | 26.7 | 5.6 | 53.4 | 20.5 | 117 | 1:3.0 | 14.0 | 59.0 |

TABLE 3-continued

| Example | Catalyst Amount (g) | T (°C.) | P - PSIG | SV-g propane/ g cat-hr | Reaction Time (sec) | % Con | % $CO_x$ | % Sel $C_{3=}$ | % Sel AA | % AA Yield | KgAA/ m$^3$cat- hr | P:$O_2$ | $H_2O$/P | Sel. to $C_{3=}$ + AA |
|---|---|---|---|---|---|---|---|---|---|---|---|---|---|---|
| $Mo_1V_{0.3}Nb_{0.05}Sb_{0.15}K_{0.015}$ | | | | | | | | | | | | | | |
| 22 | 2.7 | 400 | 32 | 0.19 | 0.96 | 39 | 30.1 | 7.5 | 49.0 | 18.9 | 93.7 | 1:1.6 | 15.5 | 56.5 |
| Comp. 9 | 2.7 | 400 | 31 | 0.11 | 1.22 | 57 | 47.1 | 3.5 | 37.7 | 21.7 | 59.5 | 1:3.0 | 14.3 | 41.1 |

P = Propane
SV = Space Velocity
$C_{3=}$ = Propylene
AA = Acrylic Acid
% Con = percent conversion
Sel = selectivity
% $CO_x$ = percent carbon monoxide + carbon dioxide The relevant portions of Table 3 are extracted below:

| Catalyst | Example | Propane/ Oxygen mole ratio | Productivity (KgAA/m$^3$cat · hr) |
|---|---|---|---|
| $MoV_{0.2}Nb_{0.12}Ag_{0.23}$ | 13 | 2:1(1:0.5) | 292 |
| | 14 | 1:1(1:1) | 183 (propane-rich) |
| | Comp. 3 | 0.5:1(1:2) | 97 (stoichiometric) |
| | Comp. 4 | 0.33:1(1:3) | 76 (oxygen-rich) |
| $MoV_{0.3}Nb_{0.05}Sb_{0.15}Bi_{0.03}$ | 15 | 2:1(1:0.5) | 562.9 (propane-rich) |
| | Comp. 5 | 0.33:1(1:3) | 195 (oxygen-rich) |
| | 16 | 0.625:1(1:1.6) | 209.2 (propane-rich) |
| | Comp. 6 | 0.33:1(1:3) | 130.7 (oxygen-rich) |
| $MoV_{0.3}Nb_{0.05}Sb_{0.15}Ga_{0.03}$ | 17 | 0.625:1(1:1.6) | 313 (propane-rich) |
| | Comp. 7 | 0.33:1(1:3) | 229 (oxygen-rich) |
| $MoV_{0.3}Nb_{0.05}Sb_{0.15}Ag_{0.06}$ | 18 | 2:1(1:0.5) | 280 |
| | 19 | 2:1(1:0.5) | 268 |
| | 20 | 2:1(1:0.5) | 247 |
| | 21 | 0.625:1(1:1.6) | 213 (propane-rich) |
| | Comp. 8 | 0.33:1(1:3) | 117 (oxygen-rich) |
| $Mo_1V_{0.3}Nb_{0.05}Sb_{0.15}K_{0.015}$ | 22 | 0.625:1(1:1.6) | 93.7 (propane-rich) |
| | Comp. 9 | 0.33:1(1:3) | 59.5 (oxygen-rich) |

As can be seen from the data above, a feed with a more propane than the stoichiometric molar ratio, e.g., a propane:oxygen mole ratio in the range of from 2:1 to 0.625:1 (propane-rich) as in Examples 13-22 results in better productivity for acrylic acid than a feed with a stoichiometric molar ratio, e.g., a propane:oxygen mole ratio of 0.5:1 (stoichiometric) as in Comparative Example 3, or a more oxygen than the stoichiometric molar ratio, e.g., a propane:oxygen mole ratio of 0.33:1 (oxygen-rich) as in Comparative Examples 4-9, for different catalysts within the claimed invention.

The FIGURE is a simplified flowsheet illustrating an embodiment of the present invention. Line 1 is the fresh feed to the process comprising alkane, oxygen, water and carrier gases. The relative amounts of each are controlled so that when combined with the recycle stream of Line 8 (to be described below) the desired ratios for alkane+alkene:oxygen:carrier:water are achieved. Oxygen may be supplied in pure form, as air (in which case the nitrogen becomes part of the carrier gases) or in any combination of oxygen with inert or diluent gas(es).

Lines 1 and 8 are fed to the catalytic gas phase oxidation reaction section (101) where the alkane along with the alkene contained in the recycle stream from Line 8 is partially converted and oxidized to the unsaturated carboxylic acid. More alkene is also formed from the alkane along with other byproducts, such as carbon monoxide and carbon dioxide. The reaction product stream (Line 2) is conveyed to a quenching section (102) where the carboxylic acid, some high-boiling byproducts and some of the water are condensed and removed with the quenching liquid, typically water, in Line 3 which goes to the product separation and purification section (not shown). The non-condensed gases are removed from the quenching section by Line 4 which contains virtually all of the unreacted alkane, the alkene formed by the reaction, carbon oxides, unreacted oxygen and other low-boiling byproducts.

Line 4 is split into two lines, Line 5 and Line 6. Line 5 is a small purge stream to control the accumulation of diluent materials in the recycle loop. Line 6 conveys recycled gas to a carbon dioxide removal section (103) in which carbon dioxide is selectively removed from the other recycled gases by any of the well-known methods for this process, such as the Benson process. Removal of the carbon dioxide allows a smaller purge in Line 5 with a resultant decrease in loss of recycled alkane and alkene components. Line 8 conveys recycled alkane and alkene gases, water, and other diluent gases back to the catalytic oxidation reaction section (101).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A method for producing an unsaturated carboxylic acid comprising:
    contacting a feed comprising propane and an oxygen-containing gas with a catalyst composition in a reaction zone under conditions which produce a product gas comprising acrylic acid, unreacted propane and byproduct propylene;
    recovering the unreacted propane and the byproduct propylene from the product gas; and
    recycling without separation of the recovered unreacted propane and the recovered byproduct propylene to the reaction zone;
wherein the propane:oxygen molar ratio of the feed is 2:1 to 0.625:1, and
wherein said catalyst composition comprises:

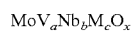

$$MoV_aNb_bM_cO_x$$

wherein Mo is molybdenum, V is vanadium, Nb is niobium and M is one or more elements selected from the group consisting of tellurium, antimony, silver, bismuth, gallium and potassium; a is 0.1 to 0.5; b is 0.1 to 0.5; c is 0.1 to 0.5; and x is determined by the valence requirements of the other components of the catalyst composition.

2. The process of claim 1 wherein the propane:oxygen molar ratio of the feed is from 2:1 to 1:1.

3. The process of claim 1 wherein M is tellurium.

4. The process of claim 1 wherein M is tellurium and antimony.

5. The process of claim 1 wherein M is silver.

6. The process of claim 1 wherein M is silver and antimony.

7. The process of claim 1 wherein M is bismuth and antimony.

8. The process of claim 1 wherein M is gallium and antimony.

9. The process of claim 1 wherein M is potassium and antimony.

10. The process of claim 1 wherein the catalyst composition is $MoV_{0.3}Nb_{0.12}Te_{0.23}$.

11. The process of claim 1 wherein the catalyst composition is $MoV_{0.3}Nb_{0.05}Sb_{0.15}Te_{0.06}$ or $MoV_{0.3}Nb_{0.05}Sb_{0.09}Te_{0.09}$.

12. The process of claim 1 wherein the catalyst composition is $MoV_{0.3}Nb_{0.05}Sb_{0.15}Ag_{0.06}$.

13. The process of claim 1 wherein the amount of propylene which is recycled to the reactor feed is within a propane:propylene ratio of 1:0.02 to 1:0.2.

14. The process of claim 13 wherein the propane:propylene ratio is 1:0.04 to 1:0.1.

15. The process of claim 1 wherein the contact time for the reactants is in the range of from 0.1 to 2.0 seconds.

16. The process of claim 15 wherein the contact time is in the range of from 0.2 to 1.0 seconds.

17. The process of claim 1 wherein inert gas may be used as a carrier medium.

18. The process of claim 17 wherein the inert gas is carbon dioxide, methane, nitrogen, argon or helium.

19. The process of claim 17 wherein the molar ratio of propane:carrier is in the range from 0.1:1 to 10:1.

20. The process of claim 1 wherein the feed additionally comprises carbon dioxide, methane or water.

21. The process of claim 20 wherein the water is present as steam and the molar ratio of alkane:steam is in the range from 0.05:1 to 10:1.

22. The process of claim 1 wherein the reaction temperature is 320-450° C.

23. The process of claim 21 wherein the reaction temperature is 350-410° C.

24. The process of claim 1 wherein the reaction pressure is 0 to 75 psig.

25. The process of claim 24 wherein the reaction pressure is 5 to 50 psig.

26. The process of claim 1, wherein b is 0.01 to 0.2.

* * * * *